(12) United States Patent
Brunsman (10) Patent No.: US 9,415,146 B2
(45) Date of Patent: Aug. 16, 2016

(54) SYSTEM AND METHOD FOR REMOVING A CRYPOROTECTANT FROM A LIQUID

(75) Inventor: Alan Robert Brunsman, Yellow Springs, OH (US)

(73) Assignee: Cook General Biotechnology LLC, Indianapolis, IN (US)

( * ) Notice: Subject to any disclaimer, the term of this patent is extended or adjusted under 35 U.S.C. 154(b) by 981 days.

(21) Appl. No.: 13/421,275

(22) Filed: Mar. 15, 2012

(65) Prior Publication Data

US 2012/0168376 A1   Jul. 5, 2012

Related U.S. Application Data

(63) Continuation of application No. 12/500,077, filed on Jul. 9, 2009, now abandoned.

(60) Provisional application No. 61/079,282, filed on Jul. 9, 2008.

(51) Int. Cl.
*A61M 1/16* (2006.01)
*B01D 61/34* (2006.01)
*A61M 1/02* (2006.01)
*B01D 61/32* (2006.01)
*A61M 1/36* (2006.01)

(52) U.S. Cl.
CPC ........... *A61M 1/0281* (2013.01); *A61M 1/1682* (2014.02); *B01D 61/32* (2013.01); *A61M 1/3669* (2013.01)

(58) Field of Classification Search
None
See application file for complete search history.

(56) References Cited

U.S. PATENT DOCUMENTS

| 5,110,477 A | 5/1992 | Howard et al. |
| 5,295,505 A | 3/1994 | Polaschegg et al. |
| 6,126,831 A | 10/2000 | Goldau et al. |
| 6,869,758 B1 | 3/2005 | Gao et al. |
| 6,939,471 B2 | 9/2005 | Gross et al. |
| 2003/0195454 A1 | 10/2003 | Wariar et al. |

OTHER PUBLICATIONS

Brochure "Online Clearance Monitoring, Haemodialysis Machines", Fresenius Medical Care, May 2003.

*Primary Examiner* — Krishnan S Menon
(74) *Attorney, Agent, or Firm* — Woodard Emhardt Moriarty McNett & Henry LLP (57) ABSTRACT

A system for removing cryoprotectant from a cryoprotectant-containing liquid stored a container comprises a cryoprotectant removal device that receives the cryoprotectant-containing liquid and a cryoprotectant-free dialysate liquid and that is operable to transfer cryoprotectant to the dialysate liquid. A differential conductivity device is arranged to continuously measure the difference in conductivity between dialysate liquid entering the device and dialysate liquid that has received cryoprotectant transferred by the dialyzer discharged from the device. A controller is operable to control the flow of the liquids through the device in response to the measured difference in conductivity, and particularly to stop the flow of the cryoprotectant-containing liquid when the measured differential conductivity indicates that the cryoprotectant has been substantially removed from the liquid.

15 Claims, 6 Drawing Sheets

SYSTEM AND METHOD FOR REMOVING A CRYOPOROTECTANT FROM A LIQUID

REFERENCE TO RELATED APPLICATION

The present application claims priority to co-pending application Ser. No. 12/500,077, filed on Jul. 9, 2009, and which claimed priority to provisional application No. 61/079,282, filed on Jul. 9, 2008, all in the name of the present inventor, and entitled "System for Detecting the Presence of a Substance in a Fluid." The disclosure of the application No. 61/079,282 is incorporated herein by reference.

BACKGROUND

The present disclosure concerns systems and methods for detecting the presence of substances in a liquid, such as blood and other bodily liquids. One application of the system and method disclosed herein is to detect the presence of preservation substances, such as DMSO, in a cryogenically-treated blood sample that is being treated to remove the DMSO.

It is known to utilize various cryoprotectants, such as dimethyl sulfoxide (DMSO), during cryopreservation cells. Use of a cryoprotectant is essential to prevent cryoinjury to the cells, such as from the formation of intracellular ice crystals during freezing. Thus, in stem cell transplant treatments, for instance, the stem cells are obtained and frozen, to be later thawed for periodic treatments of a patient affected by cancer or other diseases. In some prior treatments, the frozen-thawed stem cells are injected into the patient, along with the cryoprotectant, because there have been no effective ways to remove the cryoprotectant without losing a significant amount of stems cells or otherwise contaminating them. However, at room or body temperature, certain cryoprotectants, such as DMSO, are known to be toxic to cells as well as the patient. For instance, DMSO is known to cause ill effects in patients, ranging from fever and nausea to violent cramping. In some cases, the presences of cryoprotectant may endanger the patient's life. The potentially dangerous effects of cryoprotectants on the patient has tempered the desirability of using frozen and banked cells or liquids of any type.

One common method for removal of cryoprotectant has been mechanical removal, typically in the form of centrifugation followed by resuspension in a media to remove the cryoprotectant by dilution. However, the mechanical forces introduces during centrifugation result in osmotic stress and cell clumping/lysing, particular for fragile cells. Moreover, the generally open nature of centrifugation may result in bacterial or viral contamination of the cell preparation.

In order to address these problems a closed system has been developed as disclosed in U.S. Pat. No. 6,869,758 (the '758 Patent), assigned to the University of Kentucky Research Foundation. The disclosure of the '758 Patent is incorporated herein by reference. The '758 Patent discloses passing the cryoprotectant-containing liquid through at least one semipermeable hollow fiber membrane contained in a hollow module in a first direction to contact the hollow fiber membrane on at least one interior surface. Concurrently, a liquid which is substantially free of cryoprotectant is passed through the hollow module in a second direction (opposite the first direction) so that the cryoprotectant-free liquid contacts the semipermeable hollow fiber membrane on at least one exterior surface. A diffusion gradient is thus created that transfers the cryoprotectant from the cryoprotectant-containing liquid to the cryoprotectant-free liquid for subsequent removal.

Figure 2:
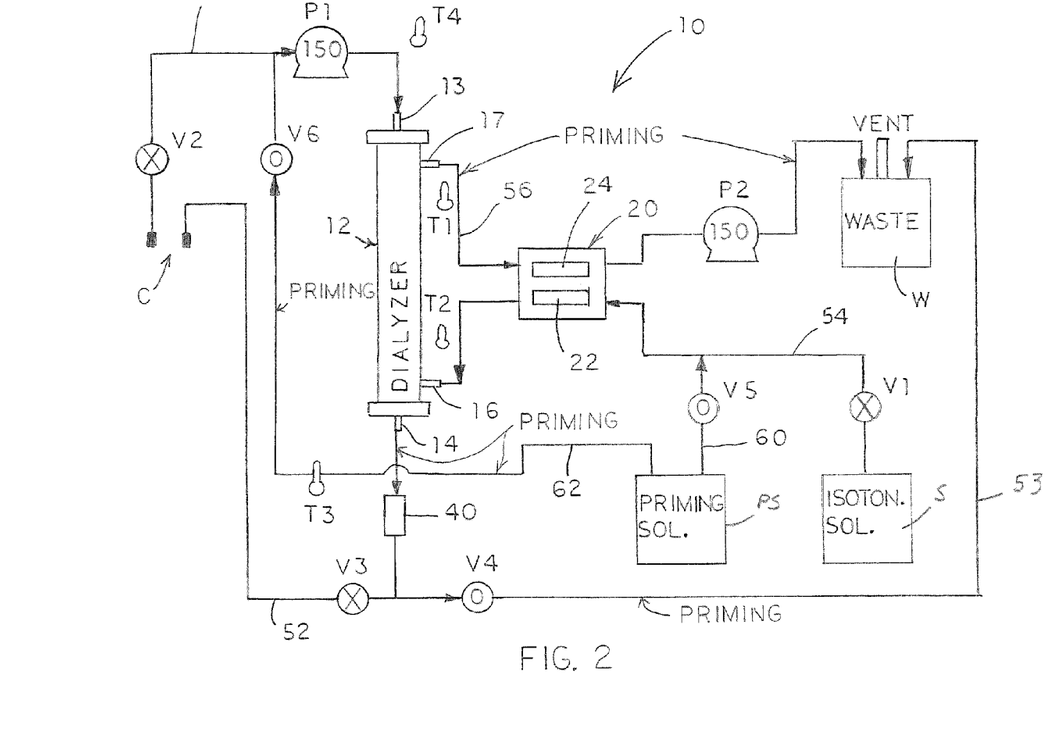
FIG. 2 is a diagram of a closed system for removing cryoprotectant from a liquid, incorporating the conductivity cell shown in FIG. 1, with the system in a first state for priming the system.

Thus, in the treatment of a frozen-thawed cell suspension containing a cryoprotectant, the hollow module and semipermeable hollow fiber membrane disclosed in the '758 Patent can be connected directly to the source of the suspension. In the case of frozen-thawed blood, the device disclosed in the '758 Patent can be connected to the blood bag in a closed system. The system may incorporate a series of pumps and valves to move the cell suspension liquid and the cryoprotectant-free liquid through the system. Details of one such system are shown in FIG. 2 and described herein.

The system disclosed in the '758 Patent provides a completely closed system for the effective removal of cryoprotectant from a liquid. Since the system relies upon diffusion and the dialysis process, there is no damage to the desired cells if the process is optimally performed. Moreover, the process retains a significant quantity of the original frozen-thawed liquid, again if optimally performed. In order to achieve optimal performance, it is desirable that the cryoprotectant removal process continue only for as long as necessary to reduce the presence of cryoprotectant in the cell suspension to a suitable level. While the closed system is less harmful to the desired cells than the prior mechanical methods, "overtreatment" of the cells can cause damage and reduce the quantity of viable cells. On the other hand, "under treatment" does not remove enough of the cryoprotectant, so that the damaging effects of the cryoprotectant remain. Thus, there is a need for a system and method for determining when the dialysis process is complete.

SUMMARY

According to one aspect of the invention, a system is provided for removing cryoprotectant from a cryoprotectant-containing liquid stored a container that comprises a cryoprotectant removal device that receives the cryoprotectant-containing liquid and a cryoprotectant-free dialysate liquid and that is operable to transfer cryoprotectant to the dialysate liquid. A differential conductivity device is arranged to continuously measure the difference in conductivity between dialysate liquid entering the device and dialysate liquid that has received cryoprotectant transferred by the dialyzer discharged from the device. A controller is operable to control the flow of the liquids through the device in response to the measured difference in conductivity, and particularly to stop the flow of the cryoprotectant-containing liquid when the measured differential conductivity indicates that the cryoprotectant has been substantially removed from the liquid.

In a further aspect, the cryoprotectant removing device is a dialyzer having a first inlet to receive the cryoprotectant-containing liquid, a first outlet for discharge of the cryoprotectant-liquid, a second inlet to receive a cryoprotectant-free dialysate liquid and a second outlet for discharge of the cryoprotectant-free liquid, the dialyzer forming a diffusion gradient between the cryoprotectant-containing liquid and the cryoprotectant-free liquid. The system further comprises an outlet fluid line connected to the first inlet and connectable to an outlet of the container, and an inlet fluid line connected to the first outlet and connectable to an inlet of the container, the outlet and inlet fluid lines forming a first fluid circuit between the container of the cryoprotectant-containing liquid and the dialyzer. A second outlet fluid line is connected between the source of dialysate liquid and the second inlet, and a discharge fluid line is connected to the second outlet and connectable to a waste container, the second outlet fluid line and the discharge fluid line forming a second fluid circuit between the source of dialysate liquid and the dialyzer.

A first pump is disposed in the first fluid circuit for controlling the flow of the cryoprotectant-containing liquid through the first fluid circuit, and a second pump is disposed in the second fluid circuit for controlling the flow of the dialysate liquid through the second fluid circuit. In one feature, the differential conductivity device is disposed between the second outlet fluid line and the discharge fluid line and is operable to measure the difference in conductivity between dialysate liquid flowing through the second outlet fluid line and dialysate liquid that has received cryoprotectant transferred by the dialyzer flowing through the discharge fluid line. The controller is configured to control the operation of the first and/or second pump in response to the measured difference in conductivity.

A method is provided for removing cryoprotectant from a liquid which comprising the step of passing a cryoprotectant-containing liquid and a cryoprotectant-free liquid through a cryoprotectant removal device configured to transfer cryoprotectant from the cryoprotectant-containing liquid to the cryoprotectant-free liquid. In one feature, the method includes measuring the differential conductivity between cryoprotectant-free liquid entering the device and cryoprotectant-free liquid discharged from the device after receiving cryoprotectant transferred within the device. The method further contemplates controlling the flow of the cryoprotectant-containing liquid and/or the cryoprotectant-free liquid through the device in response to the measured differential conductivity.

DESCRIPTION OF THE EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Conductivity Cells

Figure 1:
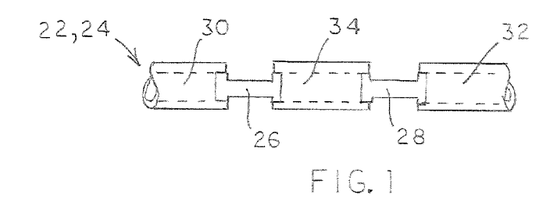
FIG. 1 is a side view of a conductivity cell for use with a closed system for removing cryoprotectant from a liquid.

The present invention contemplates the integration of conductivity cells, such as the cells 22, 24 depicted in FIG. 1, within closed system 10 shown in FIG. 2 for removal of cryoprotectant from a liquid, such as blood or a cell suspension. As shown in FIG. 1, the conductivity cells 22, 24 include flow-through conductivity electrodes 26 and 28 that are coupled to tubing 30, 32. The tubing from part of the closed system 10, as explained herein. The electrodes are separated by tubing 34 by a predetermined distance to achieve a desired conductivity cell constant K. In one specific embodiment, the electrodes are stainless steel tubing, having a length of about 4.0 cm, an outer diameter of about 0.48 cm. and an inner diameter of about 0.38 cm. The tubing 34 is sized to separate the electrodes by about 9.0 cm to achieve a cell constant of fifty. The high cell constant helps minimize the effects of conductivity cell fouling. In the specific example, the conductivity cells are configured to detect the presence of DMSO in blood. Other cell constants may be preferable for detecting other cryoprotectants in other liquids.

The electrodes are connected to a conductivity meter in a conventional manner, such as with alligator clips. Alternatively, the electrodes may incorporate contact points or wiring configured to connect to a conductivity meter. One suitable conductivity meter is the YSI® Model 32 meter. In addition, the electrodes 26, 28 may incorporate fluid fittings to facilitate connection to the existing tubing 30, 32 of the closed system 10. For instance, the ends of the electrodes 26, 28 may incorporate a barbed fitting.

Closed System for Removing Cyoprotectant from a Cryoprotectant-Containing Liquid The closed system 10 for removing cryoprotectant from a liquid may be constructed as shown in FIG. 2 to incorporate the dialyzer 12 disclosed in the '758 Patent discussed above. Although the specifics of the dialyzer 12 are found in the '758 Patent, the disclosure of which is incorporated herein by reference, certain parts of the structure are shown in the present figure. In particular, the dialyzer 12 includes a first inlet 13 and a first outlet 14, as well as a second inlet 16 and a corresponding second outlet 17. The first inlet 13 is connected to the source of the cryoprotectant-containing liquid, while the second inlet 16 is connected to a source of cryoprotectant-free liquid. The corresponding outlets 14 and 17 discharge the liquids exiting the dialyzer 12.

Figure 3:
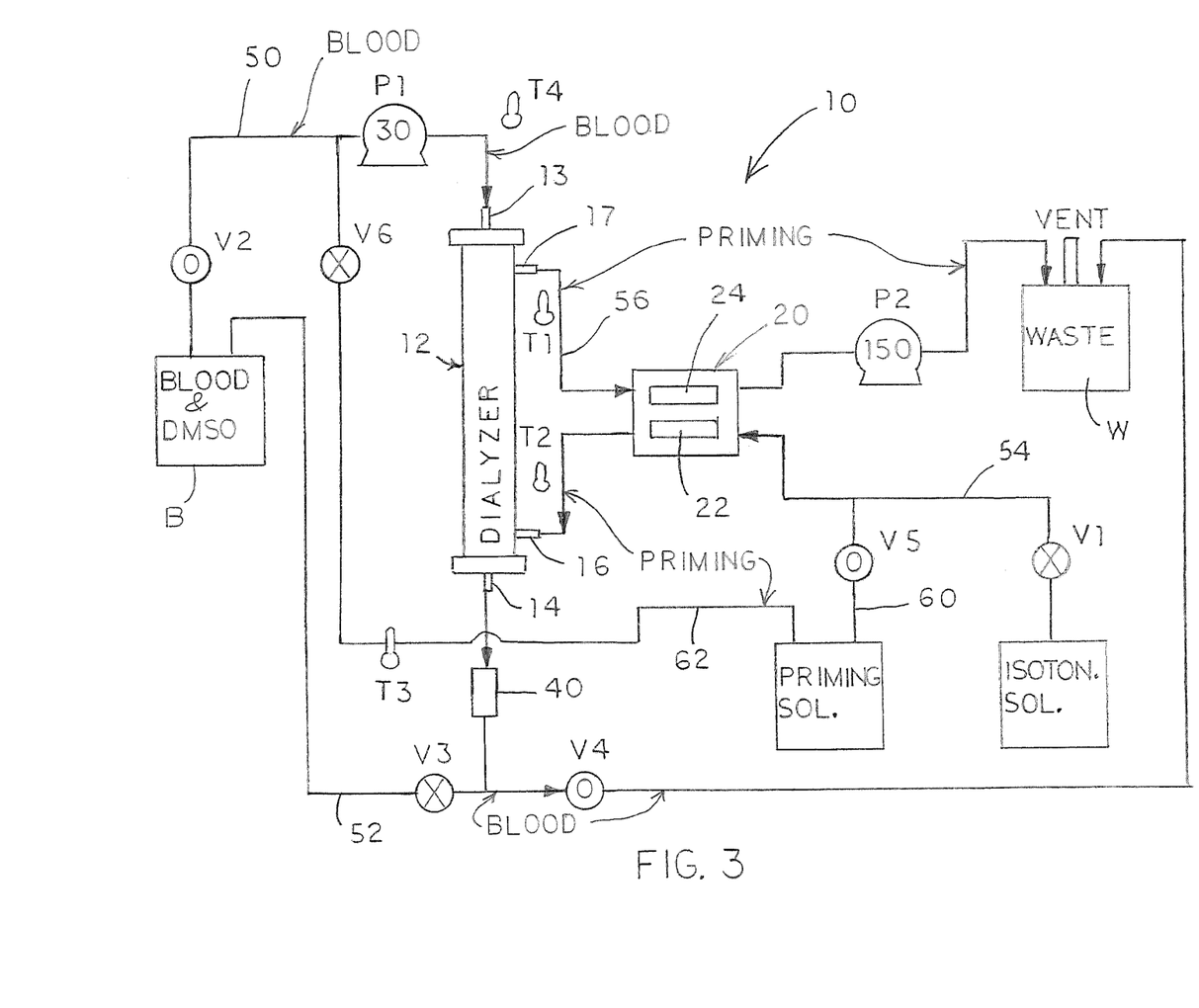
FIG. 3 is a diagram of the closed system shown in FIG. 2, with the system in a second state for commencing blood flow from a blood bag through the system.

The closed system 10 shown in FIG. 2 provides a closed fluid circuit commencing with fluid couplings C adapted to be coupled to a liquid source, such as a blood bag B as shown in FIG. 3. One coupling is connected to an outlet fluid line 50 through a valve V2, which in turn is connected to the first inlet 13 of the dialyzer 12 through a pump P1. The other coupling C is connected to a return fluid line 52 which in turn is connected to the first outlet 14 of the dialyzer 12 through a valve V3. A conductivity cell 40 may be interposed between the return fluid line 52 and the first outlet 13 of the dialyzer. As thus far described, the system 10 provides a closed fluid circuit that passes a cryoprotectant-containing liquid through the dialyzer which returns liquid to the source that has had the cryoprotectant level reduced by the dialyzer 12.

The operation of the dialyzer 12 depends upon the passage of a cryoprotectant-free liquid counter-flow to the flow of cryoprotectant-containing liquid through the dialyzer. Thus, the closed system 10 further includes a source S of a cryoprotectant-free liquid, or dialysate, such as an isotonic salt solution. This source S is connected to the second inlet 16 of the dialyzer 12 by a dialysate line 54 through a valve V1. The dialysate is discharged from the dialyzer 12 at second outlet 17 connected to dialysate discharge line 56. Since the dialysate discharged from the dialyzer includes a quantity of cryoprotectant removed from the other liquid passing through the device, the discharged dialysate is sent to a waste container W. A pump P2 is incorporated into the dialysate circuit to draw the dialysate through the dialyzer 12. The pumps P1 and P2 are sized to achieve an appropriate flow rate of the cryoprotectant-containing liquid and the dialysate for optimum performance of the dialyzer. In a specific example, the two pumps of the system 10 are adjustable flow pumps capable of operating at a maximum flow rate of 150 ml/min.

A priming circuit is also provided to prime the dialyzer 12. The circuit includes a source PS of priming solution with two output lines 60 and 62. The output line 60 is connected through a valve V5 to the dialysate line 54. The output line 62 is connected through a valve V6 to the first inlet 13 of the dialyzer 12, or more particularly to the outlet line 50 through which the cryoprotectant-containing liquid is provided. The priming solution flows through the dialyzer 12 prior to its operation on the cryoprotectant-containing liquid.

In accordance with one aspect of the invention, a differential conductivity device 20 is introduced into the dialysate circuit. In particular the device 20 includes a conductivity cell 22 connected across the outlet line 54 from the dialysate source S, and a conductivity cell 24 connected across the discharge line 56 prior to the pump P2 and waste container W. The differential conductivity device 20 generates differential conductivity readings for the dialysate entering and exiting the dialyzer 12 during operation. A third conductivity cell 40 is provided at the outlet 14 of the dialyzer 14 to measure the conductivity of the cryoprotectant-containing liquid after it has been treated in the dialyzer.

It is known that the readings produced by the conductivity cells 22, 24 and 40 will vary with temperature. In order to obtain accurate measurements the readings are temperature compensated. Thus, a temperature probe is positioned close to each conductivity cell. In particular, as shown in FIG. 2, a temperature sensor T1 is adjacent cell 22, sensor T2 is adjacent cell 24 and temperature sensor T3 adjacent cell 40. An additional temperature sensor T4 may be provided at the blood inlet to the dialyzer 12.

Operation of the Closed System
  Start-Up/Priming

At start-up, the system shown in FIG. 2 pumps a priming solution into both parts of the dialyzer. The presence of the priming solution in the various lines of the fluid circuits is indicated by the notation "Priming". In one embodiment, the priming solution is distilled water. Valve V6 is open to direct priming solution from container PS into the inlet 13 of the dialyzer, while valve V5 is open to direct priming solution into the dialysate inlet 16. Valves V1 and V2 connected to the dialysate source S and couplings C are both closed during priming of the dialyzer 12. The priming solution is pumped through the dialyzer by pumps P1 and P2, preferably at 150 ml/m. As shown in FIG. 2, the priming solution fed into the dialysate inlet 16 first passes through conductivity cell 22, while conductivity cell 24 receives the solution exiting at the dialysate outlet 17. The priming solution exiting the dialyzer at the first outlet 14 is directed by closed valve V3 and open valve V4 through fluid line 53 to the waste container W for appropriate disposal. Likewise, solution exiting through second outlet 17 is pumped into the waste container.

As the priming solution flows through the system as shown in FIG. 2, measurements at the conductivity cells 22, 24 and 40 are temperature corrected. Correction factors are determined for cells 24 and 40 that adjust the measurements at these cells to be equal to the measurement value of conductivity cell 24, since the same liquid, the priming solution, is flowing through each cell. In a preferred embodiment, the temperature and conductivity values are maintained within a predetermined range and are permitted to vary within predetermined narrow boundary values. Quick spikes in the readings could be an indication of bubbles in the system. After five minutes priming the dialyzer, the readings of the conductivity cells should become stable.

Detecting Blood Cells

Once the dialyzer 12 has been primed, a blood bag B is connected to the liquid couplings C, as shown in FIG. 3. In one embodiment, the blood contains a cryoprotectant used in a cryogenic process to store the blood sample. The cryoprotectant may be DMSO and may be in solution in the blood in varying percentages. A suitable dialysate to remove the DMSO is a phosphate buffered saline (PBS). The dialyzer 12 is configured as disclosed in the '758 Patent to remove the DMSO, returning substantially pure blood to the blood bag for subsequent use.

The state of the fluid circuit for blood detection within the system 10 is illustrated in FIG. 3. When the blood bag is attached, valve V2 is opened so blood solution is pumped into the blood inlet 13 of the dialyzer by pump P1, as indicated by the designation "Blood" in the system 10. The blood is preferably pumped at 30 psi. When the blood first starts to flow into the dialyzer, valve V3 is closed and valve V4 is opened to purge any residual priming solution from the dialyzer blood circuit through outlet 14 to the waste container W. The blood flowing through the system has a higher concentration of DMSO than the priming solution PBS. Thus, conductivity cell 40 will show the first indication of the higher resistance of blood solution versus the priming solution that had passed through the cell in the previous priming step shown in FIG. 2.

The priming solution PBS is pumped through the dialysate fluid circuit by the pump P2, since the valve V5 is open and the valve V1 to the dialysate source S is closed. The resistance measured by the conductivity cell 24 will also increase as the blood starts through the system because blood will cross the dialyzer into the priming solution present in the dialysate circuit formed by fluid lines 54 and 56. Nominally, conductivity cell 40 will indicate a higher resistance than conductivity cell 24 because the DMSO-containing blood transferred through the dialysis membrane of the dialyzer will necessarily become diluted by the priming solution already within the dialysate loop.

Blood Flow Back to Blood Bag

Figure 4:
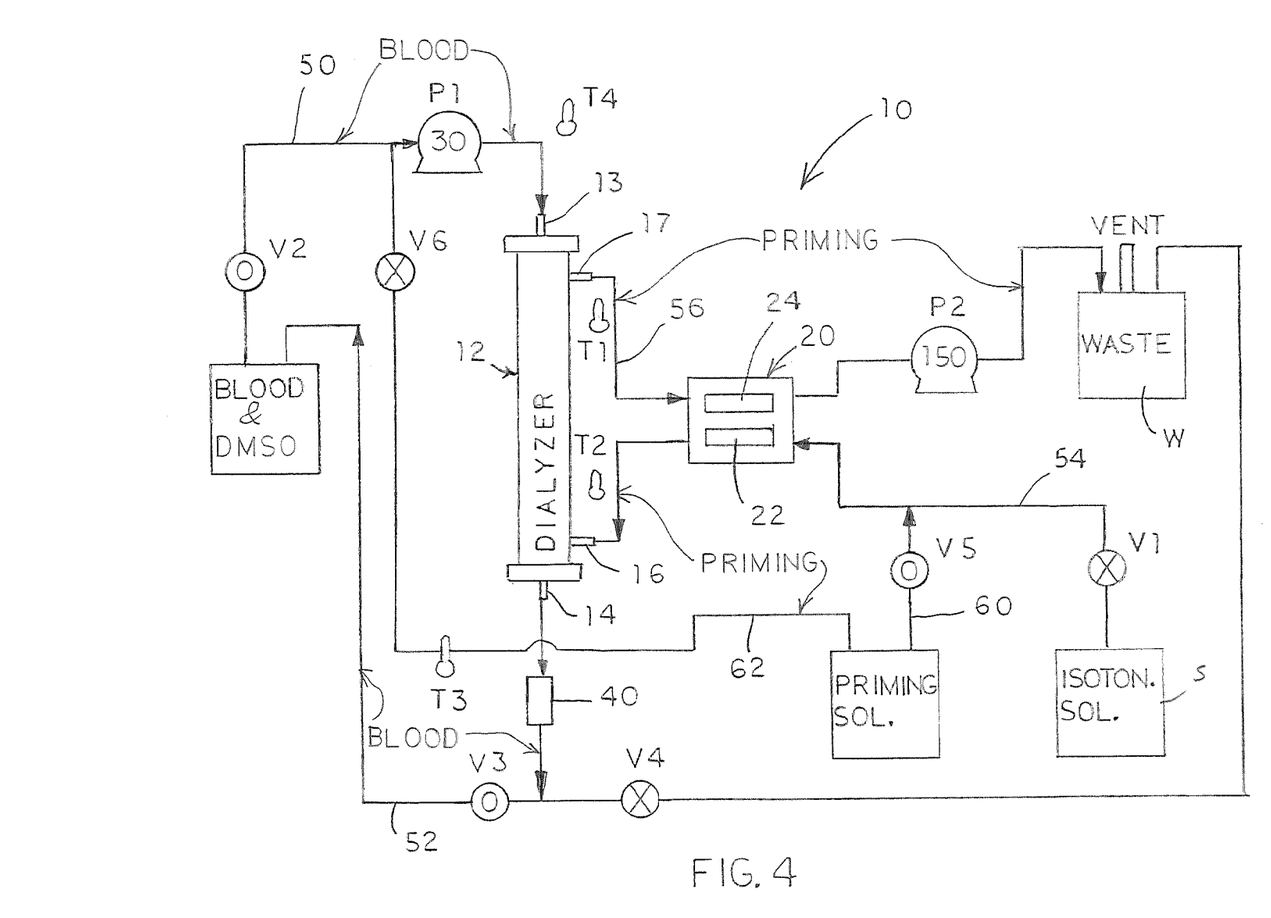
FIG. 4 is a diagram of the closed system shown in FIG. 2, with the system in a third state for directing blood flow back to the blood bag.

A change in measurement reading at conductivity cell 40 indicates when the blood has arrived at the cell, meaning that the blood has passed through the dialyzer 12. At this point, the blood flow is redirected back to the blood bag by closing valves V4 and opening valve V3, as shown in FIG. 4. It should be noted that as in the prior blood detection step, the priming solution continues to be pumped through the dialysate circuit and into the waste container at 150 psi. The priming solution is not adapted to extract the DMSO from the blood.

As the blood continues to flow through the dialyzer, the difference of the conductivity measurements between conductivity cells 22 and 24 will approach a predetermined value that is near zero. A near-zero differential conductivity means that the dialysate circuit is fully primed and ready to receive the dialysate from the source S.

Figure 5:
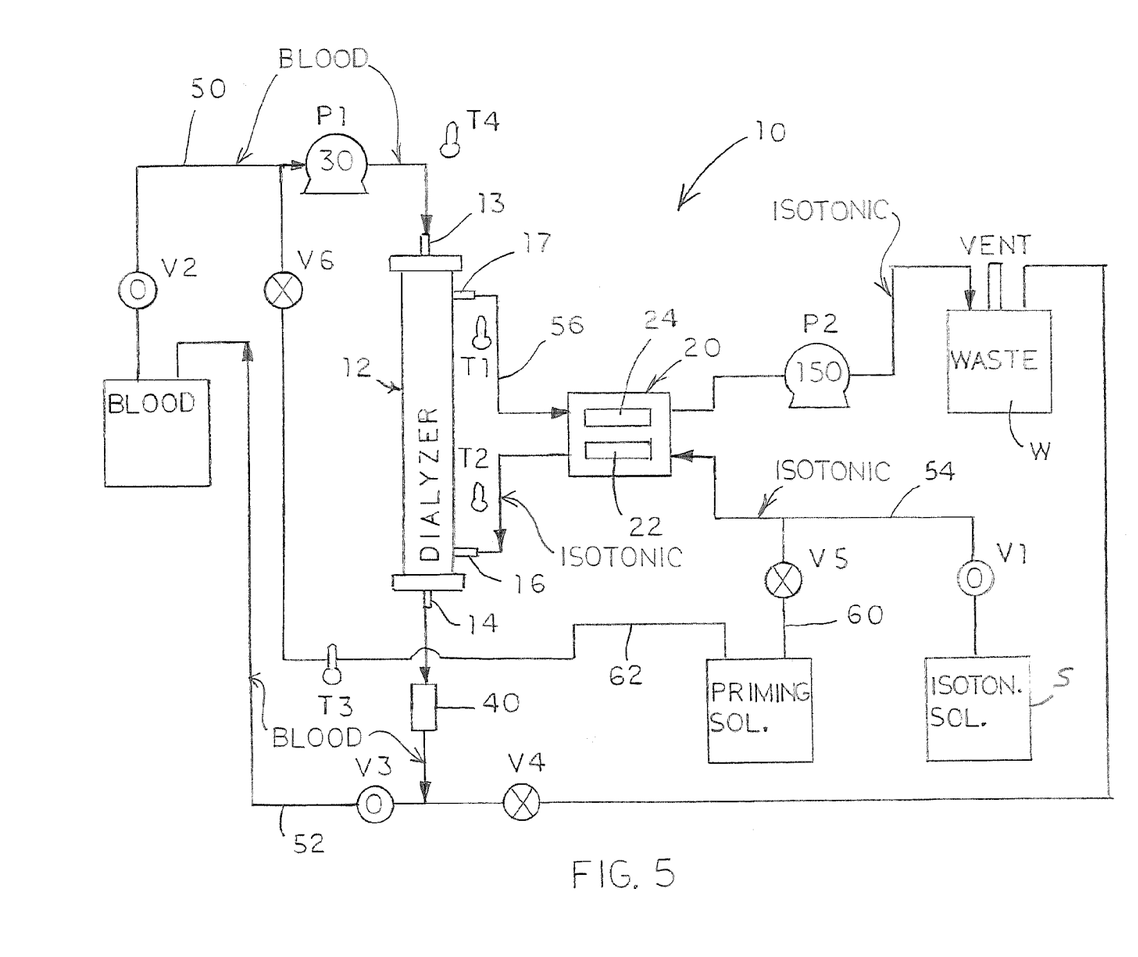
FIG. 5 is a diagram of the closed system shown in FIG. 2, with the system in a subsequent state for directing flow of dialysate through the system.

When the differential conductivity between cells 22 and 24 reaches the predetermined value, valve V5 is closed to terminate flow of priming solution through the system, as shown in FIG. 5. (Valve V6 may also be closed). Valve V1 is then opened to direct the dialysate PBS through the dialysate circuit of fluid lines 54 and 56, as indicated by the designation "Isotonic". When the isotonic solution is flowed through the distillate side of the dialyzer 12 the differential conductivity measurements will follow the same pattern as for the priming solution. Thus, the difference in measurements at conductivity cells 22 and 24 will show the removal of the DMSO and the conductivity values registered by conductivity cell 40 at the blood outlet 14 will reflect the changes to DMSO concentration in the blood solution.

By continuing the flow of blood solution and isotonic solution through the dialyzer as shown in the FIG. 5, the viable cells in the blood solution can be concentrated. The integral of the area under the temperature compensated conductivity curve for conductivity cell 40 should indicate the concentration of DMSO-free blood cells being returned to the blood bag. It is contemplated that the measurement of the conductivity cell 40 will reach a predetermined value indicative of removal of all or substantially all of the DMSO from the blood solution.

Shut Down

Figure 6:
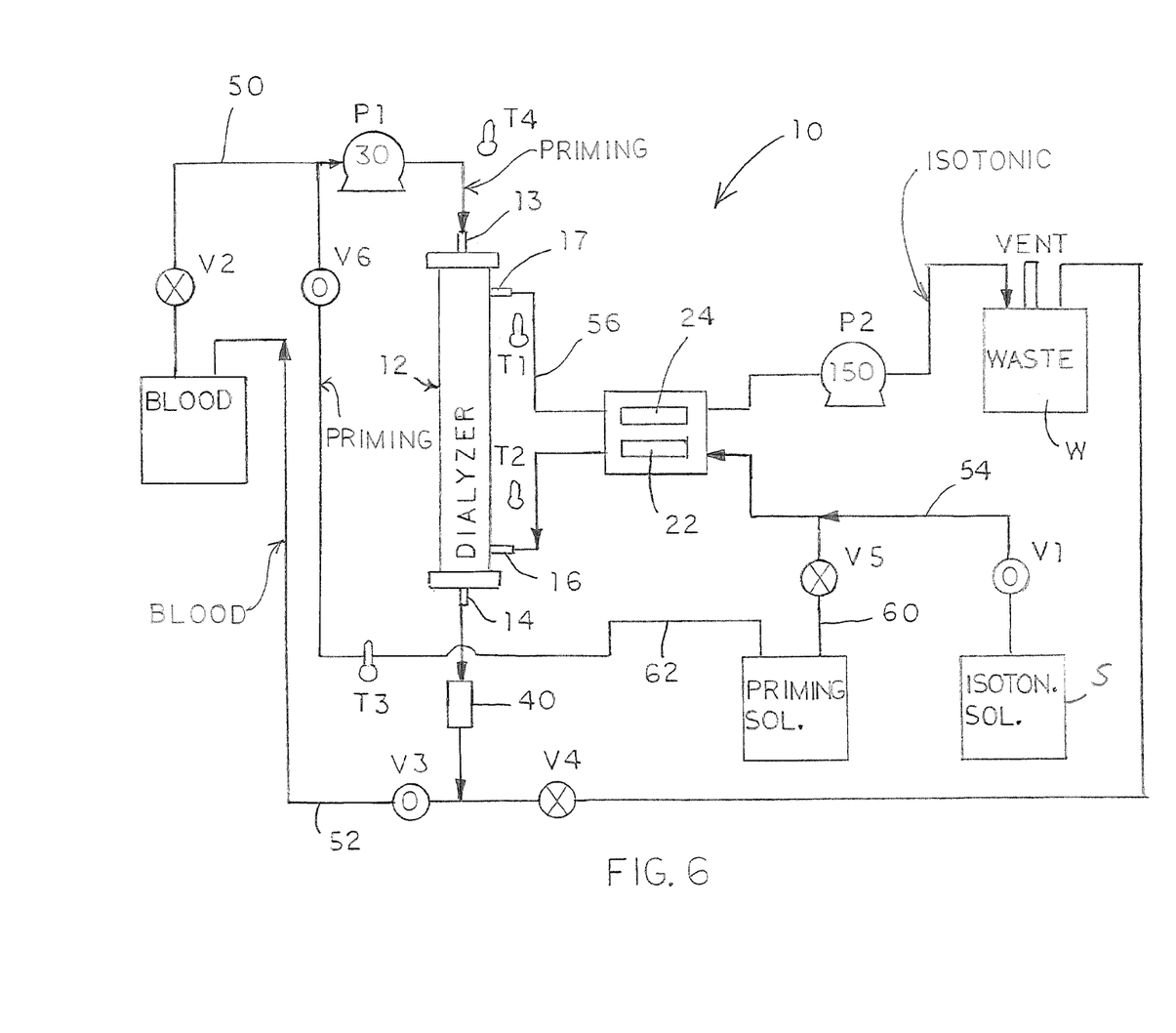
FIG. 6 is a diagram of the closed system shown in FIG. 2, with the system in a fifth state for recovering blood cells remaining in the system after the prior steps.

The conductivity cells can be used to detect the process of pushing viable cells from the dialyzer into the blood bag. In the system 10 is configured to push substantially all of the available viable cells into the blood bag using the priming solution. As shown in FIG. 6, valve V2 is closed to terminate blood flow to inlet 13, since the blood solution has been substantially purified. Valve V6 is then opened so that priming solution will flow into the inlet 13 behind the blood cells within the dialyzer 12. The isotonic solution continues to flow through the distallate circuit 54, 56 and to the waste container W. This progress of the process is indicated by conductivity changes in cells 24 and 40 to determine when valve V3 should be closed. In other words, when the conductivity measurements of conductivity cell 40 changes from the conductivity value for purified blood to the conductivity value for priming solution, it can be determined that all of the blood cells have been pushed out of the dialyzer. A similar change will be reflected at conductivity cell 24, although of a lesser magnitude, as blood cross-over into the dialysate circuit ceases.

Flow Reversal

Figure 7:
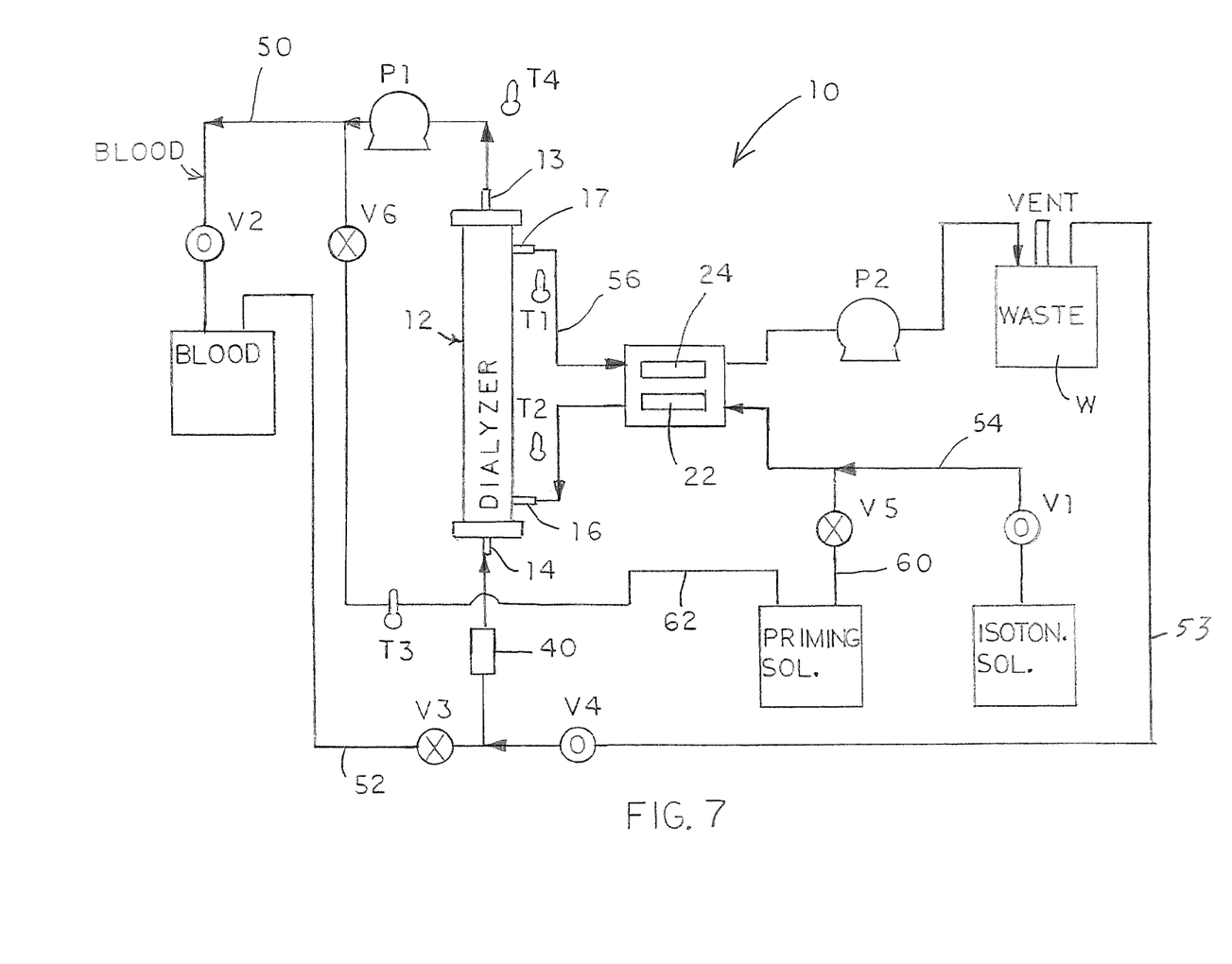
FIG. 7 is a diagram of the closed system shown in FIG. 2, with the system in a further state for recovering additional blood cells remaining in the system after the prior steps.

In a final step, the flow of pump P1 is reversed to pushing any blood cells remaining in the outlet line 50 back into the blood bag B. Thus, as shown in FIG. 7, valve V2 is opened, pump P1 is reversed, and valve V4 is opened to permit flow through the pump behind the blood cells. Flow of the isotonic solution through the dialyzer is ceased by stopping pump P2, while valves V5 and V6 are closed to terminate any priming solution flow. Thus, there will be no indication of activity at the conductivity cells 22 and 24. However, conductivity cell 40 will measure the conductivity changes from isotonic solution to priming solution, which may be used to indicate a stopping point for the process. Alternatively, the duration of the process may be limited to a predetermined time believed to be sufficient to return all viable blood cells to the blood container. This can be achieved in one embodiment by counting steps of the stepper motor driving pump P1, or by a direct time measurement to indicate when to de-energize the pump.

In certain cases, some of the blood returning to the blood bag through fluid line 52 can be immediately drawn back through the system through outlet line 50. This phenomenon can lead to a false indication of a reduction in DMSO in the blood. This occurrence can be prevented by segmenting the blood bag B that will prevent the returning "clean" blood from displacing the untreated blood remaining in the bag. In one approach, a baffle is created between the ports on the blood bag to prevent any cross-contamination. Other approaches may be implemented to ensure that all of the untreated blood in the blood bag B flows through the closed system 10 before the conductivity cells indicate a DMSO level indicative that the DMSO has been substantially removed from the blood.

It is contemplated that the sequence of opening and closing the valves V1-V6 and activating/de-activating pumps P1 and P2 can be controlled by a master controller. The controller receives signals from the conductivity cells 22, 24 and 40, as well as from the temperature sensors T1-T3, and generates control signals for the opening and closing the valves and for energizing, de-energizing and controlling flow rate and direction of the pumps P1 and P2. The controller may be analog with appropriate circuitry to evaluate measurement differences between cells and between cell measurements and threshold values.

Preferably, the components are digital and the controller is a programmable microcontroller. The digital controller can adjust the conductivity measurements generated by each conductivity cell in relation to the temperature measured by the adjacent temperature sensor. Adjusted values for the conductivity cells 22 and 24 can be used to generate the differential conductivity values used to determine when the cryoprotectant has been substantially removed from the blood. The adjusted values of all the cells can also be compared as described above to determine when the priming step has completed or when substantially all of the blood cells have been returned to the blood bag B.

The controller can also be configured to compare the differential and actual conductivity values to the various thresholds used to determine when one step is complete and another is to begin. The controller may permit user input to change the threshold values based on a particular cryoprotectant, cryoprotectant-containing liquid, dialysate or priming solution. Alternatively, or additionally, the controller may incorporate a data base of stored values that can be selected by identifying the particular combination of liquids. In addition to storing threshold values, the controller may also store the desired pump flow rates for the various steps of operation of the system 10.

It is further contemplated that the controller may be configured to monitor the rate of change in conductivity or differential conductivity at the differential conductivity device 20 as an indication of the rate or removal of cryoprotectant from the blood. In some circumstances, removal that occurs too rapidly can damage the blood cells. Thus, when the rate of change of conductivity or differential conductivity exceeds a predetermined threshold value the controller can alter the flow through the system 10, such as by reducing the flow rate of one or both of the pumps P1 and P2, to thereby protect the blood cells from rapid osmolality change.

Conductivity tests using the conductivity cell disclosed herein have been conducted to establish baseline values for certain substances and to evaluate the change in these values with temperature. For instance, tests for distilled water show a conductivity of 1.10E-07 mohs at 10° C. and an essentially linear 2.43% change in conductivity per each degree of temperature change. Similar tests on a 10% DMSO solution show initial conductivity of 5.34E-02 mohs and a rate of change of 2.10%. The conductivity at 10° C. increases to 6.48E-02 mohs for a 2.5% DMSO solution while the rate of change with temperature decreases to 1.97%. Similar tests for a 4.5% PBS solution show a conductivity at 10° C. of 3.93E-04 mohs and a rate of change of 1.76%, with the conductivity decreasing to 7.20E-05 mohs and rate of change increasing to 1.84% for a 0.9% PBS solution. The conductivity values for sucrose are 3.50E-07 mohs and 2.40%.

These test results reveal a difference in magnitude of conductivity values among the various substances flowing through the closed system 10 and the differential conductivity device 20. Thus, the differential conductivity readings used to determine when the blood is substantially free of cryoprotectant will be very pronounced initially since the lower conductivity pure dialysate PBS will be flowing through the cell 22 and the much higher conductivity PBS-DMSO solution exiting the dialyzer 12 will be flowing through the second cell 24. The amount of DMSO purged from the blood flowing through the dialyzer 12 decreases with each pass of the blood through the system so that the conductivity of the liquid flowing through the second cell 24 will gradually decrease to match the conductivity of the pure dialysate PBS at cell 22.

The closed system 10, the differential conductivity device 20 and the conductivity cell 40, as well as the protocol disclosed herein, can be used very effectively to remove cryoprotectant from a quantity of blood that has been previously frozen and then thawed. The same system and protocol can be used to remove other cryoprotectants from blood, such as glycerol, provided the conductivity values are different enough from the baseline liquids and/or that the conductivity cells are sensitive enough to measure more subtle differences in conductivity. Moreover, the present system 10 and the protocol described above can be used to monitor the removal of other substances from a particular liquid, again provided the conductivity values and change in conductivity are readily detectable by the conductivity cells.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A system for removing cryoprotectant from a cryoprotectant-containing liquid stored in a container, the system comprising: a dialyzer having a first inlet to receive the cryoprotectant-containing liquid, a first outlet for discharge of the cryoprotectant-containing liquid, a second inlet to receive a cryoprotectant-free dialysate liquid and a second outlet for discharge of the cryoprotectant-free liquid, said dialyzer forming a diffusion gradient between said cryoprotectant-containing liquid and the cryoprotectant-free liquid;
   a first fluid circuit between the container of the cryo-protectant containing liquid and said dialyzer, said first fluid circuit including;
      a first fluid line connected to said first inlet and connectable to an outlet of the container;
      a first valve disposed in said first fluid line, said first valve openable to permit and closable to prevent flow of cryoprotectant-containing liquid from the container to said dialyzer;
      an inlet fluid line connected to said first outlet of said dialyzer and connectable to an inlet of the container; and
      a first pump configured to pump liquid through said first fluid circuit in a first direction from said inlet of said dialyzer to said first outlet of said dialyzer, said first pump also configured to pump liquid through said first fluid circuit in a second direction from said first outlet of said dialyzer to said inlet of said dialyzer;
   a source of cryoprotectant-free dialysate liquid capable of receiving cryoprotectant transferred through said diffusion gradient within said dialyzer;
   a second fluid circuit between the source of dialysate liquid and said dialyzer, said second fluid circuit including;
      a second fluid line connected between said source of dialysate liquid and said second inlet of said dialyzer;
      a second valve disposed in said second fluid line, said second valve openable to permit and closable to prevent flow of dialysate liquid from said source to said dialyzer; and
      a discharge fluid line connected to said second outlet of said dialyzer and connectable to a waste container;
   a source of a priming solution for preparing said dialyzer;
   a priming fluid circuit between said source of priming solution and said dialyzer, said priming fluid circuit including;
      a first priming fluid line connected between said source of priming solution and said first inlet of said dialyzer;
      a third valve disposed in said first priming fluid line, said third valve openable to permit and closable to prevent flow of priming solution from said source of priming solution to said dialyzer; and
      a second priming fluid line connected between said source of priming solution and said second inlet of said dialyzer and a fourth valve disposed in said second priming fluid line, said fourth valve openable to permit and closable to prevent flow of priming solution from said source of priming solution to said dialyzer;
   a differential conductivity device disposed between said second fluid line and said discharge fluid line and operable to measure the difference in conductivity between dialysate liquid flowing through said second fluid line and dialysate liquid that has received cryoprotectant transferred by said dialyzer flowing through said discharge fluid line; and
   a controller for controlling the opening and closing of said first, second, third and fourth, valves in response to the measured difference in conductivity, and wherein said controller is operable to control the direction of flow from said first pump in response to the measured difference in conductivity.

2. The system for removing cryoprotectant according to claim 1, further comprising:
   a first temperature sensor adjacent said differential conductivity device and arranged to measure the temperature of liquid flowing through said second fluid line; and
   a second temperature sensor adjacent said differential conductivity device and arranged to measure the temperature of liquid flowing through said discharge fluid line, wherein said controller is further configured to adjust the measured difference in conductivity as a function of the temperature sensed by said first and second temperature sensors.

3. The system for removing cryoprotectant according to claim 1, wherein:
   said second fluid circuit includes a second pump for controlling fluid flow therethrough;
   said second priming fluid line intersects said second fluid circuit so that said second pump is operable to flow said priming solution through said dialyzer and so that said priming solution flows through said differential conductivity device; and
   said controller is configured for controlling the operation of said first and second pump in response to the measured difference in conductivity.

4. The system for removing cryoprotectant according to claim 1, further comprising:
   a conductivity cell disposed in said inlet fluid line, said conductivity cell arranged to measure the conductivity of liquid flowing through said inlet fluid line;
   a waste fluid line intersecting said inlet fluid line between said conductivity cell and the inlet to the container of the cryoprotectant-containing liquid, said waste fluid line connectable to a waste container; and
   a fifth valve disposed in said waste fluid line between said inlet fluid line and the waste container, said fifth valve openable to permit and closable to prevent flow of liquid from said dialyzer to the waste container, and wherein said controller is configured to open or close said fifth valve in response to the measured conductivity of liquid flowing through said inlet fluid line.

5. The system for removing cryoprotectant according to claim 4, further comprising:
a third temperature sensor adjacent said conductivity cell and arranged to measure the temperature of liquid flowing through said inlet fluid line, wherein said controller is further configured to adjust the measured conductivity as a function of the temperature sensed by said third temperature sensor.

6. The system for removing cryoprotectant according to claim 1, the system also comprising a container having an inlet port attached to said inlet fluid line and an outlet port attached to said first fluid line.

7. The system for removing cryoprotectant according to claim 6, wherein said container further comprising a baffle between said inlet port and said outlet port.

8. The system for removing cryoprotectant according to claim 4, further comprising a sixth valve disposed in said inlet fluid line, said sixth valve openable to permit and closable to prevent flow of liquid from said dialyzer to said inlet of said container, and wherein said controller is configured to open or close said sixth valve in response to the measured conductivity of liquid flowing through said inlet fluid line.

9. The system for removing cryoprotectant according to claim 1, wherein said first pump has a variable flow rate, and wherein said controller is configured to monitor the rate of change in conductivity or differential conductivity at said differential conductivity device and adjust the flow rate of said first pump according to the measured rate of change in conductivity or differential conductivity at said differential conductivity device.

10. The system for removing cryoprotectant according to claim 3, wherein said second pump has a variable flow rate, and wherein said controller is configured to monitor the rate of change in conductivity or differential conductivity at said differential conductivity device and adjust the flow rate of said second pump according to the measured rate of change in conductivity or differential conductivity at said differential conductivity device.

11. A system for removing cryoprotectant from a cryoprotectant-containing liquid the system comprising:
a dialyzer having a first inlet to receive the cryoprotectant-containing liquid, a first outlet for discharge of the cryoprotectant-containing liquid, a second inlet to receive a cryoprotectant-free dialysate liquid and a second outlet for discharge of the cryoprotectant-free liquid, said dialyzer forming a diffusion gradient between said cryoprotectant-containing liquid and the cryoprotectant-free liquid;
a container having an inlet port and an outlet port, said container containing a cryoprotectant-containing liquid;
a first fluid circuit between the container and said dialyzer, said first fluid circuit including;
a first fluid line connected to said first inlet and connectable to said outlet port of said container;
a first valve disposed in said first fluid line, said first valve openable to permit and closable to prevent flow of cryoprotectant-containing liquid from said container to said dialyzer; and
an inlet fluid line connected to said first outlet of said dialyzer and connectable to said inlet port of said container; and a first pump configured to pump liquid through said first fluid circuit in a first direction from said inlet of said dialyzer to said first outlet of said dialyzer, said first pump also configured to pump liquid through said first fluid circuit in a second direction from said first outlet of said dialyzer to said inlet of said dialyzer;
a source of cryoprotectant-free dialysate liquid capable of receiving cryoprotectant transferred through said diffusion gradient within said dialyzer;
a second fluid circuit between the source of dialysate liquid and said dialyzer, said second fluid circuit including;
a second fluid line connected between said source of dialysate liquid and said second inlet of said dialyzer;
a second valve disposed in said second fluid line, said second valve openable to permit and closable to prevent flow of dialysate liquid from said source to said dialyzer; and
a discharge fluid line connected to said second outlet of said dialyzer and connectable to a waste container;
a source of a priming solution for preparing said dialyzer;
a priming fluid circuit between said source of priming solution and said dialyzer, said priming fluid circuit including;
a first priming fluid line connected between said source of priming solution and said first inlet of said dialyzer;
a third valve disposed in said first priming fluid line, said third valve openable to permit and closable to prevent flow of priming solution from said source of priming solution to said dialyzer; and
a second priming fluid line connected between said source of priming solution and said second inlet of said dialyzer and a fourth valve disposed in said second priming fluid line, said fourth valve openable to permit and closable to prevent flow of priming solution from said source of priming solution to said dialyzer;
a differential conductivity device disposed between said second fluid line and said discharge fluid line and operable to measure the difference in conductivity between dialysate liquid flowing through said second fluid line and dialysate liquid that has received cryoprotectant transferred by said dialyzer flowing through said discharge fluid line; and
a controller for controlling the opening and closing of said first, second, third and fourth valves in response to the measured difference in conductivity, and wherein said controller is operable to control the direction of flow from said first pump in response to the measured difference in conductivity, such that said first pump is operable to return a portion of said cryoprotectant containing liquid remaining in said first fluid line to said container by pushing said portion of said cryoprotectant containing liquid in said second direction through said outlet port of said container.

12. The system for removing cryoprotectant according to claim 11, wherein:
said first priming fluid line intersects said first fluid circuit so that said first pump is operable to flow said priming solution through said dialyzer;
said second fluid circuit includes a second pump for controlling fluid flow therethrough;
said second priming fluid line intersects said second fluid circuit so that said second pump is operable to flow said priming solution through said dialyzer and so that said priming solution flows through said differential conductivity device; and said controller is configured for controlling the operation of said first and second pump in response to the measured difference in conductivity.

13. The system for removing cryoprotectant according to claim 12, wherein said first pump has a variable flow rate, said second pump has a variable flow rate, and wherein said controller is configured to monitor the rate of change in conductivity or differential conductivity at said differential conductivity device and adjust the flow rates of said first pump and said second pump according to the measured rate of change in conductivity or differential conductivity at said differential conductivity device.

14. The system for removing cryoprotectant according to claim 11, further comprising:
- a conductivity cell disposed in said inlet fluid line, said conductivity cell arranged to measure the conductivity of liquid flowing through said inlet fluid line;
- a waste fluid line intersecting said inlet fluid line between said conductivity cell and the inlet to the container of the cryoprotectant-containing liquid, said waste fluid line connectable to a waste container; and
- a fifth valve disposed in said waste fluid line between said inlet fluid line and the waste container, said fifth valve openable to permit and closable to prevent flow of liquid from said dialyzer to the waste container, and wherein said controller is configured to open or close said fifth valve in response to the measured conductivity of liquid flowing through said inlet fluid line.

15. The system for removing cryoprotectant according to claim 11, wherein said container further comprising a baffle between said inlet port and said outlet port.

* * * * *